(12) United States Patent
Bisacchi et al.

(10) Patent No.: US 6,713,467 B2
(45) Date of Patent: Mar. 30, 2004

(54) ACID DERIVATIVES USEFUL AS SERINE PROTEASE INHIBITORS

(75) Inventors: Gregory S. Bisacchi, Ringoes, NJ (US); James C. Sutton, Princeton Junction, NJ (US); Shung C. Wu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 73 days.

(21) Appl. No.: 10/035,714

(22) Filed: Nov. 7, 2001

(65) Prior Publication Data

US 2002/0151545 A1 Oct. 17, 2002

Related U.S. Application Data

(60) Provisional application No. 60/246,391, filed on Nov. 7, 2000, and provisional application No. 60/246,392, filed on Nov. 7, 2000.

(51) Int. Cl.[7] ............... A61K 31/33; A61K 31/401; C07D 213/00; C07D 207/00
(52) U.S. Cl. .............. 514/183; 514/212.01; 514/277; 514/315; 514/356; 514/349; 514/336; 514/405; 514/422; 546/193; 546/314; 546/315; 546/318; 548/400; 548/517; 548/530; 548/579
(58) Field of Search ............ 514/183, 212.01, 514/277, 315, 356, 349, 336, 408, 422; 546/193, 314, 315, 318; 548/400, 517, 530, 579

(56) References Cited

U.S. PATENT DOCUMENTS

| 5,612,341 A | 3/1997 | Lee et al. ............ 514/253 |
| 6,248,767 B1 | 6/2001 | Blok et al. ............ 514/380 |

FOREIGN PATENT DOCUMENTS

| EP | 0206567 | 12/1986 |
| JP | 3-7277 | 1/1991 |
| WO | WO 96/40111 | 12/1996 |
| WO | WO 97/31910 | 9/1997 |
| WO | WO 98/57937 | 12/1998 |
| WO | 9933460 | * 7/1999 |
| WO | WO02/34711 A1 | 5/2002 |

OTHER PUBLICATIONS

Kondo et al., Chem. Pharm. Cull. 42(1) pp. 62–66 (1994).
Takahai et al., J. Chem. Soc. Perkin Trans. 1, (1993) pp. 1473–1479.
Xie, et al., J. Med. Chem., (1995) 38, pp. 3003–3008.

* cited by examiner

*Primary Examiner*—Mukund J. Shah
*Assistant Examiner*—Sudhaker B. Patel
(74) *Attorney, Agent, or Firm*—Anastasia P. Winslo; Jing S Belfield

(57) ABSTRACT

Compounds of formula I and II,

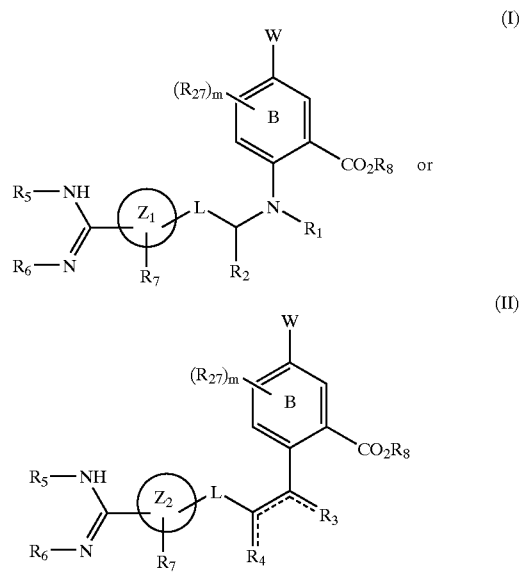

or pharmaceutically-acceptable salts thereof, are useful as inhibitors of Factor VIIa, Factor IXa, Factor Xa, Factor FXIa, tryptase, and urokinase, wherein ring B is phenyl or pyridyl, L is a linker, and $R_1$–$R_{27}$, W, $Z_1$, and $Z_2$ are as defined in the specification.

9 Claims, No Drawings

ACID DERIVATIVES USEFUL AS SERINE PROTEASE INHIBITORS

RELATED APPLICATIONS

This application claims the benefit of U.S. Provisional Application Nos. 60/246,391 and 60/246,392, both filed Nov. 7, 2000, the contents of which are incorporated herein by reference.

FIELD OF THE INVENTION

The present invention relates to acid derivatives that are inhibitors of serine proteases such as Factor VIIa, Factor IXa, Factor Xa, Factor FXIa, tryptase, and urokinase. These acid derivatives are useful as anticoagulants in treating and preventing cardiovascular diseases, as anti-inflammatory agents, and as metastasis inhibitors in treating cancer.

BACKGROUND OF THE INVENTION

Under normal conditions, the coagulation system is naturally balanced in favor of anticoagulation by a number of proteins circulating in the blood. These proteins include antithrombin III, a serine-protease inhibitor, and protein C, a vitamin-K dependent protein formed in the liver. When injury or trauma occurs, thrombin is produced at precise levels through an ordered series of reactions. Thrombin is a proteolytic enzyme that occupies a central position in the coagulation process. Thrombin catalyzes the conversion of fibrinogen to fibrin, is a key effector enzyme for blood clotting, and also is pivotal for other functions, such as activation of helper proteins (including Factors V and VIII and thrombomodulin), and its own activation. Disturbances in the natural balance between pro- and anti-coagulant forces may result in bleeding or thrombotic diseases.

The series of reactions leading to thrombin production involve a number of coagulation factors present in the blood as precursors (e.g., Factors VII–XII). When the coagulation system is triggered (e.g., when trauma occurs), the coagulation factors are transformed into activated factors (e.g., Factors VIIa, IXa, Xa, XIa, etc.). Factor VII forms a complex with a membrane protein called tissue factor, to which Factor VIIa tightly binds. Thus, Factor VIIa is present as a complex bound to tissue factor. When triggered, the coagulation factors and tissue factor complexes undergo an ordered chain of reactions that ultimately lead to conversion of Factor X to Factor Xa, and Factor Xa catalyzes the conversion of prothrombin to thrombin.

An elevated plasma level of coagulation factors, particularly Factor VIIa, is a risk factor for fatal myocardial infarction and associated with coronary artery disease and other abnormalities of the coagulation system, e.g., thrombosis, ischemic vascular disease, intravascular clotting, stroke, embolisms, and so forth. Accordingly, antithrombotic agents have been researched and developed for use in treating cardiovascular and other diseases. Presently established antithrombotic agents include heparin, coumarin, and aspirin, among others. There are, however, limitations with these agents. For example, both heparin and coumarin have a highly-variable dose-related response, and their anticoagulant effects must be closely monitored to avoid a risk of serious bleeding. The erratic anticoagulant response of heparin is likely due to its propensity to bind non-specifically to plasma proteins. Aspirin has a limited efficacy and at high doses presents a risk of gastrointestinal bleeding. Thrombin inhibitors and their drawbacks are further discussed in WO 96/20689 to duPont Merck Pharmaceutical Co.

As may be appreciated, those in the field of pharmaceutical research continue to seek to develop new compounds and compositions having increased effectiveness and bioavailability and/or having fewer side effects. See, e.g., Jakobsen et al., "*Inhibitors of the Tissue Factor/Factor VIIa-induced Coagulation: Synthesis and In vitro Evaluation of Novel Specific 2-aryl Substituted 4H-3,1-benzoxazin-4-ones,*" Bioorganic & Medicinal Chemistry, Vol. 8 (August 2000), at pp. 2095–2103; and J. Hirsh et al., "*Thrombosis, New Antithrombotic Agents,*" Lancet, Vol. 353 (Apr. 24, 1999), at pp. 1431–36. There is particularly an interest in developing agents that can selectively and directly inhibit key factors in the complicated coagulation process. Compounds effective in inhibiting Factor Xa are described in U.S. patent application Ser. No. 09/478,632, filed Jan. 6, 2000, Ser. No. 09/633,751, filed Aug. 7, 2000, and Ser. No. 09/496,571, filed Feb. 2, 2000. Compounds effective in inhibiting Factors VIIa, Xa, as well as tryptase and urokinase are described in U.S. patent application Ser. No. 09/458,847, filed Dec. 13, 1999. The above referenced '632, '751, '571, and '847 applications show lactam compounds and are each assigned to the present assignee with common inventors herewith. Factor Xa inhibitors are also disclosed in PCT applic. WO 98/57937 to the duPont Merck Pharmaceutical Co.

PCT patent application WO 99/41231 to Ono Pharmaceuticals Inc., ("Ono") discloses a series of amidino derivatives such as 2-(3-(4-amidinophenylcarbamoyl)-naphthalen-2-yl)-5-((2,2-methylpropyl)carbamoyl benzoic acid, which are claimed to be Factor VIIa inhibitors. The Ono application is discussed in Kohrt et al., "*An Efficient Synthesis of 2-(3-(4-Amidinophenylcarbamoyl)naphthalen-2-yl)-5-((2,2-methylpropyl)carbamoyl benzoic acid: a Factor VIIa Inhibitor Discovered by the Ono Pharmaceutical Company,*" Tetrahedron Letters, Vol. 41 (June 2000), at pp. 6041–44, which reports that Ono fails to fully describe an effective method for making the titled compound. Inhibitors of Factor VIIa are also reported in WO 01/44172 to Axys Pharm. Inc. PCT patent application WO 98/47876 to Akzo Novel N. V., published Oct. 29, 1998, discloses certain bicyclic groups such as isoquinoline groups which reportedly are advantageous for promoting pharmacological properties, and isoquinoline-containing compounds are disclosed in WO 94/29273 to SmithKline Beecham Corp. Biphenyl compounds and/or acid substituted bicyclic compounds are also disclosed in U.S. Pat. Nos. 5,612,341, 6,248,767 B1, 3,995, 045, EP patent application 0 206 567 A2 to Warner Lambert Co., and WO 01/70678 to Merck Patent GmbH.

The patents, patent applications, and articles cited above are incorporated herein by reference.

The present invention provides acid-based compounds useful as inhibitors of Factor VIIa, Factor IXa, Factor Xa, Factor FXIa, tryptase, and urokinase.

SUMMARY OF THE INVENTION

Acid derivatives are provided that are inhibitors of serine proteases having the Formula I or II:

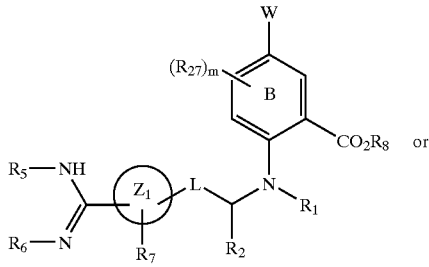

(I)

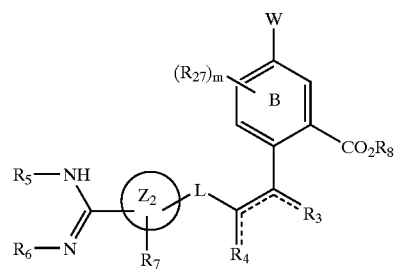

(II)

or a pharmaceutically-acceptable salt, hydrate or prodrug thereof, in which:

ring B is phenyl or pyridyl;

W is selected from $C_{2-10}$alkyl, $C_{2-10}$alkenyl, substituted $C_{2-10}$alkyl, substituted $C_{2-10}$alkenyl, —C(=O)NR$_9$R$_{10}$, —OR$_9$, —CO$_2$R$_9$, —C(=O)R$_9$, —SR$_9$, —S(O)$_p$R$_9$, —NR$_9$R$_{10}$, —NR$_9$SO$_2$R$_{10}$, —NR$_9$CO$_2$R$_{10}$, —NR$_9$C(=O)R$_{10}$, —SO$_2$NR$_9$R$_{10}$, —NR$_{9a}$SO$_2$NR$_4$R$_5$, —NR$_{9a}$C(=O)NR$_4$R$_5$, heterocyclo, heteroaryl, aryl, and cycloalkyl;

$Z_1$ is selected from a 5 to 7-membered monocyclic or 8 to 11-membered bicyclic aryl, heteroaryl, heterocyclo, or cycloalkyl;

$Z_2$ is a fully saturated carbocyclic or heterocyclic 5–7 membered monocyclic or 7–11 membered bicyclic ring;

L is —(CR$_{18}$R$_{19}$)$_s$—Y—(CR$_{18a}$R$_{19a}$)$_t$—;

Y is selected from —C(↑O), —C(=O)NR$_{13}$—, —NR$_{13}$C(=O)—, —NR$_{13}$CR$_{14}$R$_{15}$—, —CR$_{14}$R$_{15}$—NR$_{13}$—, and —CR$_{13}$R$_{14}$—CR$_{15}$R$_{16}$—;

$R_1$ and $R_2$ (i) are independently hydrogen, alkyl, substituted alkyl, alkenyl, substituted alkenyl, alkynyl, substituted alkynyl, aryl, heteroaryl, heterocyclo, or cycloalkyl; or (ii) are taken together to form a five-to-seven membered fully saturated heterocyclo optionally substituted with one to two $R_{26}$;

$R_3$ and R4 (i) are independently selected from hydrogen, alkyl, substituted alkyl, alkenyl, substituted alkenyl, heteroaryl, aryl, heterocyclo, and cycloalkyl; or (ii) are taken together to form an aryl, heteroaryl, cycloalkyl, or heterocyclo, wherein when $R_3$ and $R_4$ individually or together form a heteroaryl, aryl, heterocyclo, or cycloalkyl, said cyclic group is optionally substituted with up to two $R_{26}$;

$R_5$ and $R_6$ are independently selected from hydrogen, alkyl, substituted alkyl, hydroxy, alkoxy, substituted alkoxy, —C(=O)H, acyl, —CO$_2$H, and alkoxycarbonyl, provided that at least one of $R_5$ and $R_6$ is hydrogen;

$R_7$ is attached to any available carbon or nitrogen atom of Z and is selected from hydrogen, halogen, alkyl, substituted alkyl, alkenyl, substituted alkenyl, alkynyl, substituted alkynyl, heteroalkyl, substituted heteroalkyl, —C(=O)H, acyl, —CO$_2$H, alkoxycarbonyl, sulfonyl, sulfonamido, aryl, heteroaryl, heterocyclo, or cycloalkyl, except when Z is phenyl, W is OCH$_3$, s is 0 and Y is —CH$_2$—CH$_2$—, then $R_7$ is not phenyloxy;

$R_8$ is hydrogen, alkyl, substituted alkyl, heteroaryl, aryl, heterocyclo, cycloalkyl, or alkyl substituted with —OC(=O)R$_{24}$ or —OC(=O)O—R$_{24}$, wherein R$_{24}$ is alkyl, substituted alkyl, or cycloalkyl, provided that $R_8$ is not phenyl when W is methoxy;

$R_9$, $R_{9a}$, and $R_{10}$ are (i) independently selected from hydrogen, alkyl, substituted alkyl, alkenyl, substituted alkenyl, alkynyl, substituted alkynyl, heteroalkyl, substituted heteroalkyl, aryl, heteroaryl, heterocyclo, and cycloalkyl; or alternatively (ii) $R_9$ and $R_{10}$ may be taken together to form a five-to-seven membered heteroaryl or heterocyclo, except when W is —S(O)$_p$R$_9$, then $R_9$ is not hydrogen;

$R_{13}$, $R_{14}$, $R_{15}$, $R_{16}$, $R_{18}$, $R_{18a}$, $R_{19}$, and $R_{19a}$ are selected from hydrogen, lower alkyl, hydroxy, or lower alkyl substituted with hydroxy or halogen;

$R_{26}$ and $R_{27}$ (i) are at each occurrence independently selected from hydrogen, OR$_{30}$, NR$_{31}$R$_{32}$, NR$_{31}$SO$_2$R$_{32a}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl, or (ii) two of $R_{26}$ and/or two of $R_{27}$ may be taken together to form a fused benzo ring, a fused heteroaryl, a fused cycloalkyl, or a fused heterocyclo other than a five or six membered heterocyclo having as its heteroatoms two oxygen atoms;

$R_{30}$ at each occurrence is selected from hydrogen, alkyl, substituted alkyl, alkenyl, substituted alkenyl, cycloalkyl, and phenyl;

$R_{31}$ and $R_{32}$ at each occurrence are independently selected from hydrogen, alkyl, substituted alkyl, alkenyl, substituted alkenyl, and cycloalkyl;

$R_{32a}$ is alkyl, substituted alkyl, alkenyl, substituted alkenyl, or cycloalkyl;

m is 0, 1 or 2 when ring B is phenyl and 0 or 1 when ring B is pyridyl;

p and q are independently 1 or 2; and s and t are independently 0, 1 or 2.

Included within the scope of the invention are pharmaceutical compositions for treating a serine protease disease, an inflammatory or immune condition, or cancer, comprising at least one compound of formula I or II, or a pharmaceutically acceptable salt, hydrate or prodrug thereof, and a pharmaceutically acceptable carrier or diluent. Also included in the invention are methods of treating such diseases comprising administering to a mammal in need of such treatment at least one compound of formula I or II, or a pharmaceutically acceptable salt, hydrate or prodrug thereof. Further included in the invention are compositions for use as anticoagulants during the preparation, use, storage, or fractionation of blood and methods of maintaining blood in the fluid phase during its preparation, use, storage, or fractionation.

DETAILED DESCRIPTION OF THE INVENTION

The following are definitions of terms used in this specification. The initial definition provided for a group or term herein applies to that group or term throughout this specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo, alkenyl, alkynyl, nitro, cyano, hydroxy, alkoxy, alkylthio, —$CO_2$H, —C(=O)H, —$CO_2$-alkyl, —C(=O)alkyl, —S(O)$_2$(alkyl), keto (=O), aryl, heteroaryl, heterocyclo, and cycloalkyl, including phenyl, benzyl, phenylethyl, phenyloxy, and phenylthio. The substituents for "substituted alkyl" groups may also be selected from the group consisting of —NR'R", —C(=O)NR'R", —$CO_2$NR'R", —NR'$CO_2$'R", —NR'C(=O)R", —$SO_2$NR'R", and —NR'$SO_2$'R", wherein each of R' and R" is independently selected from hydrogen, alkyl, cycloalkyl, and alkyl substituted with one to two of alkenyl, halogen, haloalkyl, haloalkoxy, cyano, nitro, hydroxy, alkoxy, alkylthio, amino, alkylamino, phenyl, benzyl, phenyloxy, and benzyloxy. Alternatively, R' and R" may together form a heterocyclo or heteroaryl ring. When a substituted alkyl includes an aryl, heterocyclo, cycloalkyl, or heteroaryl substituent, said ringed systems are as defined below and thus may have zero, one, two, or three substituents, also as defined below.

When the term "alkyl" is used in conjunction with another group, e.g., arylalkyl, hydroxyalkyl, etc., the term defines with more specificity a particular substituent that a substituted alkyl will contain. For example, arylalkyl refers to a substituted alkyl group having from 1 to 12 carbon atoms and at least one aryl substituent, and "lower arylalkyl" refers to substituted alkyl groups having 1 to 4 carbon atoms and at least one aryl substituent.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene group, these groups are substituted with one to three substitutents as defined above for alkyl groups. A ringed substituent of an alkyl, alkenyl, alkynyl, alkylene, alkenylene, or alkynylene may be joined at a terminal atom or an available intermediate (branch or chain) atom and thus may comprise, for example, the groups

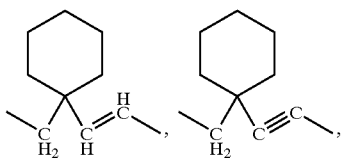

and so forth.

The term "alkoxy" refers to an alkyl group as defined above having one, two or three oxygen atoms (—O—) in the alkyl chain. For example, the term "alkoxy" includes the groups —O—$C_{1-2}$alkyl, —$C_{1-6}$alkylene-O—$C_{1-6}$alkyl, —$C_{1-4}$alkylene-O—$C_{1-4}$alkylene-O—$C_{1-4}$alkyl, O—$C_{1-4}$alkylene-O—$C_{1-4}$alkylene-O—$C_{1-4}$alkyl, and so forth.

The term "alkylthio" refers to an alkyl group as defined above bonded through one or more sulfur (—S—) atoms. For example, the term "alkylthio" includes the groups —S—$C_{1-12}$alkyl, —$S_{1-6}$alkylene-S—$C_{1-6}$alkyl, etc.

The term "alkylamino" refers to an alkyl group as defined above bonded through one or more nitrogen (—NR—) groups. The term alkylamino refers to straight and branched chain groups and thus, for example, includes the groups —NH($C_{1-12}$alkyl) and —N($C_{1-6}$alkyl)$_2$.

When a subscript is used with reference to an alkoxy, alkylthio or alkylamino, the subscript refers to the number of carbon atoms in the group in addition to heteroatoms. Thus, for example, monovalent $C_{1-2}$alkylamino includes the groups —NH—$CH_3$, —NH—$CH_2$—$CH_3$, and —N—($CH_3$)$_2$. A lower alkylamino comprises an alkylamino having from one to four carbon atoms.

When reference is made to a substituted alkoxy or alkylthio, the carbon atoms of said groups are substituted with one to three substituents as defined above for alkyl groups. When reference is made to a substituted alkylamino, the carbon and/or nitrogen atoms of these groups are substituted with one to three substitutents appropriately selected from the group of substituents recited above for alkyl groups. Additionally, the alkoxy, alkylthio, or alkylamino groups may be monovalent or bivalent. By "monovalent" it is meant that the group has a valency (i.e., power to combine with another group), of one, and by "bivalent" it is meant that the group has a valency of two. Thus, for example, a monovalent alkoxy includes groups such as —O—$C_{1-12}$alkyl and —$C_{1-6}$alkylene-O—$C_{1-6}$alkyl, whereas a bivalent alkoxy includes groups such as —O—$C_{1-12}$alkylene- and —$C_{1-6}$alkylene-O—$C_{1-6}$alkylene-, etc.

The term "heteroalkyl" is used herein to refer saturated and unsaturated straight or branched chain hydrocarbon groups having 2 to 12 carbon atoms, preferably 2 to 8 carbon atoms, wherein one, two or three carbon atoms in the straight chain are replaced by a heteroatom (O, S or N). Thus, the term "heteroalkyl" includes alkoxy, alkylthio, and alkylamino groups, as defined above, as well as alkyl groups having a combination of heteroatoms selected from O, S, or N. A "heteroalkyl" herein may be monovalent or bivalent, and for example, may comprise the groups —O—($CH_2$)$_{2-5}$NH—($CH_2$)$_2$— or —O—($CH_2$)$_{2-5}$NH—$CH_3$, etc. A "substituted heteroalkyl" has one to three substituents appropriately selected from those recited above for alkyl groups.

The term "acyl" refers to a carbonyl group

linked to an organic radical including an alkyl, alkenyl, alkynyl, substituted alkyl, substituted alkenyl, or substituted alkynyl group, as defined above.

The term "alkoxycarbonyl" refers to a carboxy or ester group

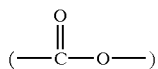

linked to an organic radical including an alkyl, alkenyl, alkynyl, substituted alkyl, substituted alkenyl, or substituted alkynyl group, as defined above.

The term "halo" or "halogen" refers to chloro, bromo, fluoro and iodo.

The term "haloalkyl" means an alkyl having one or more halo substituents, e.g., including trifluoromethyl.

The term "haloalkoxy" means an alkoxy group having one or more halo substituents. For example, "haloalkoxy" includes —OCF$_3$.

The term "sulfonyl" refers to a sulphoxide group (i.e., —S(O)$_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —SO$_2$-alkyl), or bivalent (e.g., —SO$_2$-alkylene, etc.)

The term "sulfonamide" refers to the group —S(O)$_2$NR'R", wherein R' and R" may be hydrogen or alkyl, alkenyl, substituted alkynyl, as defined above. R' and R" may be monovalent or bivalent (e.g., —SO$_2$—NH-alkylene, etc.)

The term "aryl" refers to phenyl, biphenyl, 1-naphthyl and 2-naphthyl, with phenyl being preferred. The term "aryl" includes such rings having zero, one, two or three substituents selected from the group consisting of halo, alkyl, alkenyl, alkynyl, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When an aryl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents, preferably zero or one, selected from the group consisting of halo, alkyl, alkenyl, alkynyl, nitro, cyano, oxo (=O), hydroxy, alkoxy, alkylthio, —CO$_2$H, —C(=O)H, CO$_2$-alkyl, —C(=O)alkyl, keto, =N—OH, =N—O-alkyl, heteroaryl, heterocyclo, a five or six membered ketal (i.e. 1,3-dioxolane or 1,3-dioxane), a four to seven membered carbocyclic ring, —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, a four to seven membered carbocyclic ring, heterocyclo, heteroaryl, —NR'R", —C(=O)NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a cycloalkyl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms, provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halo, alkyl, alkenyl, alkynyl, nitro, cyano, oxo, hydroxy, alkoxy, alkylthio, —CO$_2$H, —C(=O)H, CO$_2$-alkyl, —C(=O)alkyl, keto, =N—OH, =N—O-alkyl, aryl, heteroaryl, cycloalkyl, a five or six membered ketal (i.e. 1,3-dioxolane or 1,3-dioxane), —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'RR", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a heterocyclo is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, alkenyl, alkynyl, nitro, cyano, hydroxy, alkoxy, alkylthio, —$CO_2H$, —C(=O)H, $CO_2$-alkyl, —C(=O)alkyl, phenyl, benzyl, phenylethyl, phenyloxy, phenylthio, cycloalkyl, heterocyclo, a further monocyclic heteroaryl, —NR'R", —C(=O)NR'R", —$CO_2$NR'R", —NR'$CO_2$'R", —NR'C(=O)R", —$SO_2$NR'R", —NR'$SO_2$'R", and/or alkyl substituted with one to three of halo, nitro, cyano, hydroxy, alkoxy, alkylthio, —$CO_2H$, —C(=O)H, $CO_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —$CO_2$NR'R", —NR'$CO_2$'R", —NR'C(=O)R", —$SO_2$NR'R", and/or —NR'$SO_2$'R", wherein each of R' and R" is independently selected from hydrogen, alkyl, alkoxy, hydroxyalkyl, and arylalkyl, or R' and R" together form a heterocyclo or heteroaryl ring. When a heteroaryl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "carbocyclic" refers to optionally substituted aromatic or non-aromatic 3 to 7 membered monocyclic and 7 to 11 membered bicyclic groups, in which all atoms of the ring or rings are carbon atoms.

When the term "unsaturated" is used herein to refer to a ring or group, the ring or group may be fully unsaturated or partially unsaturated.

The term "metal ion" refers to alkali metal ions such as sodium, potassium or lithium and alkaline earth metal ions such as magnesium and calcium, as well as zinc and aluminum.

Whenever a bond appears in a formula as a dashed-double bond, i.e., with one bond appearing as a dash as in

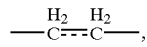

it should be understood that such bonds may be selected from single or double bonds, as appropriate given the selections for adjacent atoms and bonds. It should be further understood that one skilled in the field may make various substitutions for each of the groups recited in the claims herein, without departing from the spirit or scope of the invention. For example, one skilled in the field may replace a W group recited in the claims with a cyano, halogen, or methyl group. The linker group "L" recited in the claims may be replaced with the group —(R')$_u$—Y'—(R")$_v$— wherein Y' is a Y group recited in claim 1, is a bond, or is selected from —C(=O)—, —[C(=O)]$_2$—, —O—, —NR—, —C(=NR)—, —S(O)$_{1-2}$—, —NRC(=O)NR—, —NR$SO_2$—, or —$SO_2$NR—, wherein R is selected from alkyl, substituted alkyl, alkenyl, substituted alkenyl, a heterocyclo or carbocyclic ring, and so forth, R' and R" may comprise substituted or unsubstituted alkylene, alkenylene, or alkynylene, and u and v may be 0–4. Additionally, the acid group —$CO_2R_3$ may be joined to the phenyl or pyridyl ring B with a linker such as a methylene group or replaced with other acid functional groups such as —$SO_3H$, —P(=O)(OR)$_2$, —$SO_2$NHC(=O)R, —C(=O)NHSO$_2$R, —C(=O)NHOH, —[C(=O)]$_2$OR, or tetrazole, wherein R is hydrogen, alkyl, substituted alkyl, cycloalkyl, and so forth. Additionally, it should be understood that when a bond is represented as generally being attached to a bicyclic ring system, without indicating the precise point of attachment, the bond may be attached to any available carbon or nitrogen atom of either ring. For example, the ring systems recited as

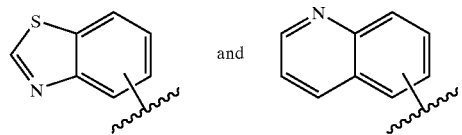

may be attached to a substrate at any available carbon atom of either the five membered or six membered rings, and the ring systems recited as

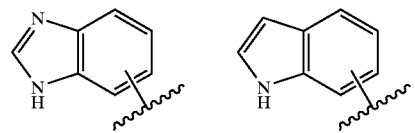

may be attached to a substrate at any available carbon atom or nitrogen atom of the five or six membered rings.

It should be further understood that for compounds of formula I and II, the linker group "L" is inserted into the formula I or II in the same direction set forth in the text. Thus, for example, if L is recited as —CH$_2$—Y—, this means the —CH$_2$— group is attached to Z, and the Y group is attached to the $C_6$ carbon atom i.e., to which $R_4$ is attached, as in:

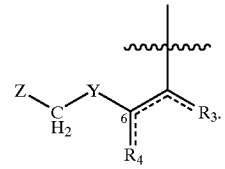

Likewise, when Y is recited as —NR$_{13}$C(=O)—, the carbonyl group C(=O) is attached to the $C_6$ carbon atom and the nitrogen group —NR$_{13}$— is attached to Z. Conversely, when Y is recited as —C(O)NR$_{13}$—, this means the carbonyl group C(=O) is attached to Z and the nitrogen group —NR$_{13}$— is attached to the $C_6$ carbon atom.

Throughout the specification, groups and substituents thereof may be chosen by one skilled in the field to provide stable moieties and compounds.

The compounds of formula I or II form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula I or II contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I or II may be formed, for example, by reacting a compound of the formula I or II with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula I or II, and/or a salt and/or solvate thereof. Various forms of prodrugs are well known in the art. For examples of such prodrug derivatives, see:

a) *Design of Prodrugs,* edited by H. Bundgaard, (Elsevier, 1985) and *Methods in Enzymology,* Vol.42, p. 309–396, edited by K. Widder, et al. (Acamedic Press, 1985);

b) *A Textbook of Drug Design and Development,* edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews,* 8, 1–38 (1992), each of which is incorporated herein by reference.

Compounds containing a carboxy group can form physiologically hydrolyzable esters which serve as prodrugs by being hydrolyzed in the body to yield formula I or II compounds per se. For example, in compounds of formula (I), prodrugs comprise compounds wherein the upper ring substituent —$CO_2R_8$ is a group that will hydrolyze in the body to compounds where said substituent is —$CO_2H$. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or II include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the formula I or II and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

The compounds of the instant invention may, for example, be in the free or hydrate form, and may be obtained by methods exemplified by the following descriptions.

Preferred Compounds

Preferred compounds of this invention are those of formula (I) or (II):

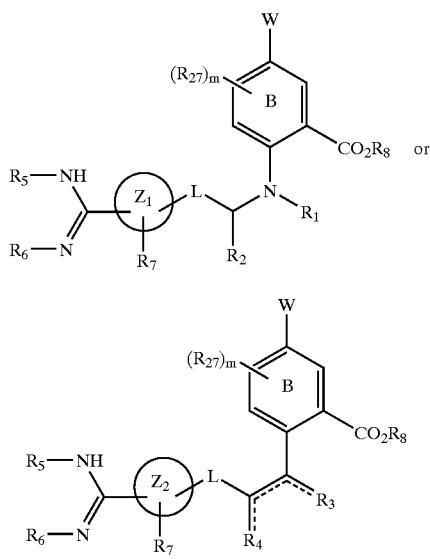

and pharmaceutically-acceptable salts, hydrates or prodrugs thereof, in which:

ring B is phenyl;

W is —C(=O)NR$_9$R$_{10}$;

L is —C(=O)—, —(CH$_2$)$_s$NHC(=O)—, —(CH$_2$)$_s$NH—CH$_2$—, or —CH$_2$—CH$_2$—,

Z$_1$ is selected from a 5 to 7-membered monocyclic or 8 to 11-membered bicyclic aryl, heteroaryl, heterocyclo, or cycloalkyl;

Z$_2$ is a fully saturated carbocyclic or heterocyclic 5 to 7 membered ring;

R$_1$ and R$_2$ (i) are independently hydrogen, alkyl, arylalkyl or aryl; or (ii) are taken together form a five-to-seven membered aryl, heteroaryl, heterocyclo, cycloalkyl, or substituted cycloalkyl optionally substituted with oxo (=O) or one to two R$_{26}$;

R$_3$ and R$_4$ (i) are independently selected from hydrogen, alkyl, substituted alkyl, alkenyl, substituted alkenyl, heteroaryl, aryl, heterocyclo, and cycloalkyl; or (ii) are taken together to form a five-to-seven membered aryl, heteroaryl, cycloalkyl, or heterocyclo, wherein when R$_3$ and R$_4$ individually or together form a heteroaryl, aryl, heterocyclo, or cycloalkyl, said cyclic group is optionally substituted with up to two R$_{26}$;

R$_5$ and R$_6$ are hydrogen;

R$_7$ is selected from hydrogen, halogen, —C(=O)NH$_2$, —C(=O)C$_{1-4}$alkyl, —NH$_2$, —NHC$_{1-4}$alkyl, —S—C$_{1-4}$alkyl, —O—C$_{1-4}$alkyl, C$_{1-4}$alkyl, C$_{1-4}$alkyl substituted with NH$_2$, and five or six membered heterocyclo or heteroaryl;

R$_8$ is hydrogen, alkyl, substituted alkyl, heteroaryl, aryl, heterocyclo, cycloalkyl, or alkyl substituted with —OC(=O)R$_{24}$ or —OC(=O)O—R$_{24}$, wherein R$_{24}$ is alkyl, substituted alkyl, or cycloalkyl, provided that R$_8$ is not phenyl when W is methoxy;

R$_9$ and R$_{10}$ are (i) independently selected from hydrogen, alkyl, substituted alkyl, alkenyl, substituted alkenyl, alkynyl, substituted alkynyl, heteroalkyl, substituted heteroalkyl, aryl, heteroaryl, heterocyclo, cycloalkyl, and cyano; or alternatively (ii) R$_9$ and R$_{10}$ may be taken together to form a five-to-seven membered heteroaryl or heterocyclo;

R$_{26}$ and R$_{27}$ are at each occurrence independently selected from hydrogen, OR$_{30}$, NR$_{31}$R$_{32}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl;

R$_{30}$ at each occurrence is selected from hydrogen, alkyl, substituted alkyl, alkenyl, substituted alkenyl, cycloalkyl, and phenyl;

R$_{31}$ and R$_{32}$ at each occurrence are independently selected from hydrogen, alkyl, substituted alkyl, alkenyl, substituted alkenyl, and cycloalkyl; and s is 0 or 1.

More preferred are compounds as immediately defined above, or pharmaceutically-acceptable salts, hydrates or prodrugs thereof, in which:

W is —C(=O)NCH(R$_{25}$)-t-butyl or —CH$_2$C(=O)NCH(R$_{25}$)-t-butyl;

L is —NHC(=O)—; and

R$_{25}$ is hydrogen or CH$_2$OH.

Further preferred compounds are those having one of the following formulae

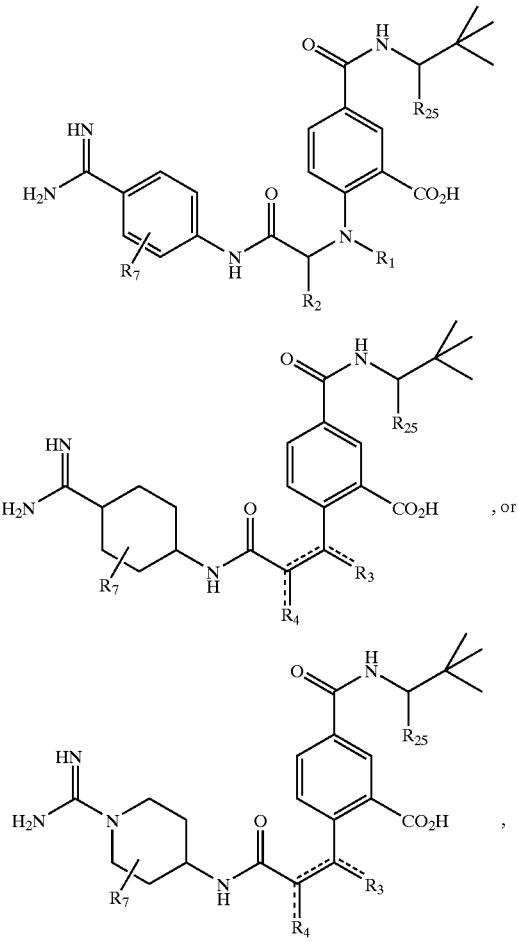

in which

R$_1$ and R$_2$ (i) are independently hydrogen, lower alkyl, arylalkyl or aryl; or (ii) are taken together form a five-to-seven membered aryl or heterocyclo optionally substituted with oxo (=O) or one to two R$_{26}$;

R$_3$ and R$_4$ (i) are independently selected from hydrogen, lower alkyl, substituted lower alkyl, alkenyl, substituted alkenyl, heteroaryl, aryl, heterocyclo, and cycloalkyl; or (ii) are taken together to form a five-to-seven membered aryl, heteroaryl, cycloalkyl, or heterocyclo, wherein when $R_3$ and $R_4$ individually or together form a heteroaryl, aryl, heterocyclo, or cycloalkyl, said cyclic group is optionally substituted with up to two $R_{26}$;

$R_7$ is selected from hydrogen, halogen, —C(=O)NH$_2$, —C(=O)C$_{1-4}$alkyl, —NH$_2$, —NHC$_{1-4}$alkyl, —S—C$_{1-4}$alkyl, —O—C$_{1-4}$alkyl, C$_{1-4}$alkyl, C$_{1-4}$alkyl substituted with NH$_2$, and five or six membered heterocyclo or heteroaryl (most preferably hydrogen);

$R_{25}$ is hydrogen or CH$_2$OH;

$R_{26}$ is hydrogen, OR$_{30}$, or NR$_{31}$R$_{32}$;

$R_{30}$ is hydrogen, lower alkyl, C$_{2-4}$alkenyl, cycloalkyl, phenyl or benzyl; and $R_{31}$ and $R_{32}$ at each occurrence are independently selected from hydrogen, lower alkyl, alkenyl, and cycloalkyl.

Methods of Preparation

The compounds of the invention may be prepared by the exemplary processes described in the following reaction schemes. Exemplary reagents and procedures for these reactions appear hereinafter and in the working Examples. Starting materials are commercially available or can be readily prepared by one of ordinary skill in the art. For all of the schemes, the groups $R_1$–$R_{27}$, W, Z, s and r are as described herein for a compound of formula I or II, unless otherwise indicated. Groups designated R', P', and P" as well as solvents, temperatures, pressures, and other reaction conditions, may readily be selected as appropriate by one of ordinary skill in the art. Additionally, one skilled in the field will appreciate that it may be advantageous in the following schemes to attach further protecting groups to the functional groups of starting materials or intermediates which then may be removed using appropriate deprotecting conditions. See, for example, Greene and Wuts, *Protecting Groups in Organic Synthesis* (John Wiley & Sons, New York 1991), incorporated herein by reference.

SCHEME A

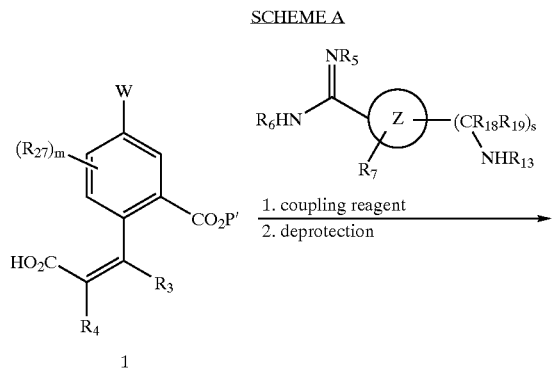

Compounds of formula IIa can be made by reacting acid 1, prepared with known methods, with an amidine having the desired Z group, i.e., NHR$_6$C(=NR$_7$)—Z—(CR$_{18}$R$_{19}$)$_s$—NHR$_{13}$. The 2-position acid group is suitably protected (P'), and the reaction is carried out in the presence of coupling reagent(s) such as DCC/HOBT/DMAP, EDC/DMAP, or DIC/HOAT to afford the corresponding amide compound. Deprotection, if desired, then affords the compound of formula IIa wherein $R_8$ is hydrogen, or the group P' may be retained wherein P' comprises the desired group $R_3$. Alternatively, the group P' may be deprotected to afford the group CO$_2$H, with the group CO$_2$H then converted to another desired $R_3$ group. To illustrate, the compound having the acid group CO$_2$H may be reacted with a halide having the desired $R_3$ group, i.e., X—R$_3$ where X is Cl, Br, or I, in the presence of base, or by the acid compound may be coupled with an alcohol such as R$_3$OH in a coupling reagent. Compound 1 can be prepared as described in WO 99/041231, incorporated herein.

SCHEME B

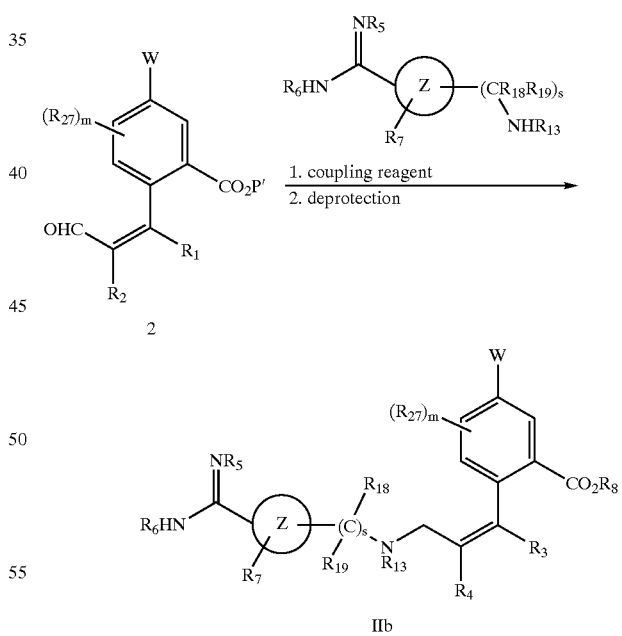

Similar to Scheme A, reaction of aldehyde 2, prepared by known methods, wherein the 2-position acid group is suitably protected (P'), with an amidine NHR$_6$C(=NR$_7$)—Z—(CR$_{18}$R$_{19}$)$_s$—NHR$_{13}$ in the presence of a reducing reagent such as sodium triacetoxyborohydride, affords the corresponding amide compound. Upon optional deprotection or further reaction or coupling as described in Scheme A, the compound of formula IIb having the desired $R_8$ group is provided. Compound 2 can be prepared as described in WO 99/041231.

SCHEME C

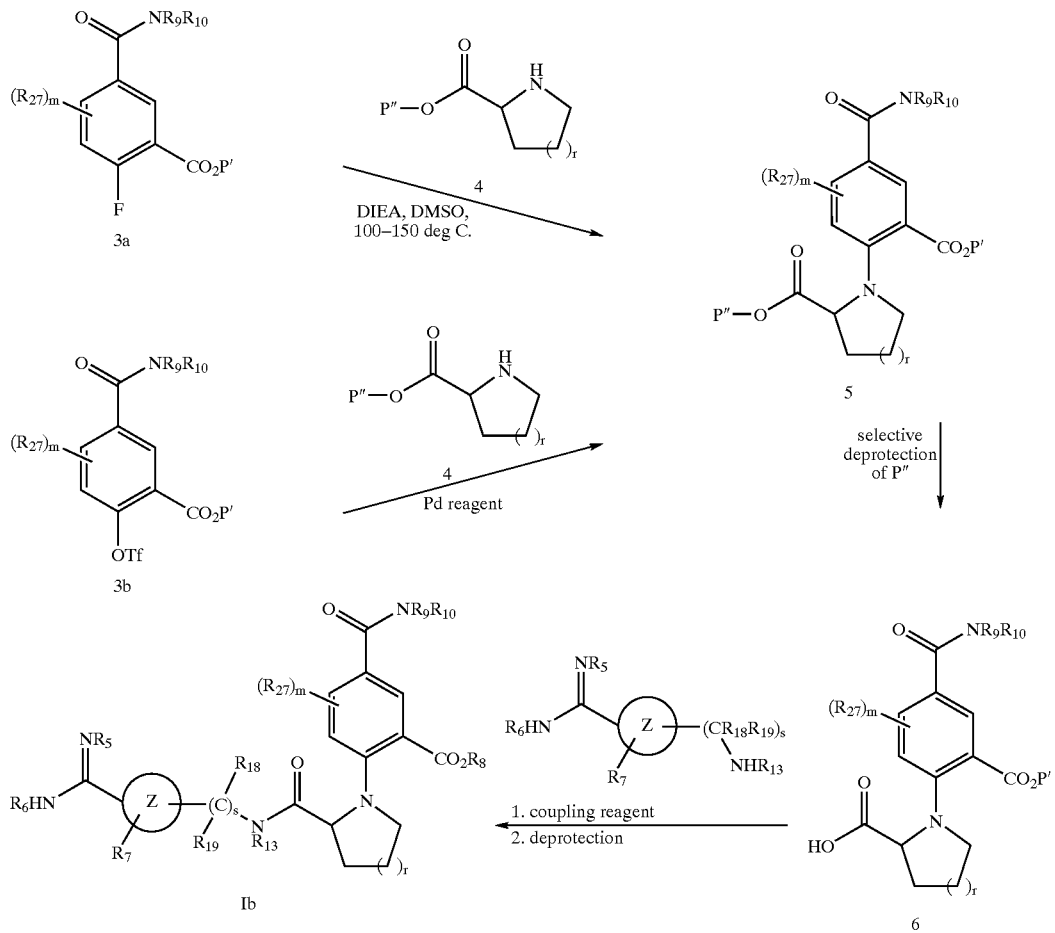

Aryl fluoride 3a is reacted with amine 4 in DMSO in the presence of a base such as DIEA to afford intermediate 5. Alternatively, triflate 3b is reacted with amine 4 in the presence of a suitable palladium reagent to afford intermediate 5. Selective deprotection of the P″ group of compound 5 affords acid 6. Acid 6 is reacted with an appropriate amidine $NHR_6C(=NR_7)-Z-(CR_{18}R_{19})_s-NHR_{13}$ in the presence of suitable coupling reagents followed by deprotection, if desired to achieve the selected group $R_8$ (as described in Scheme A) to afford the compound of formula Ib.

SCHEME D

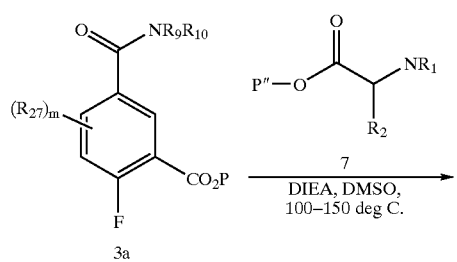

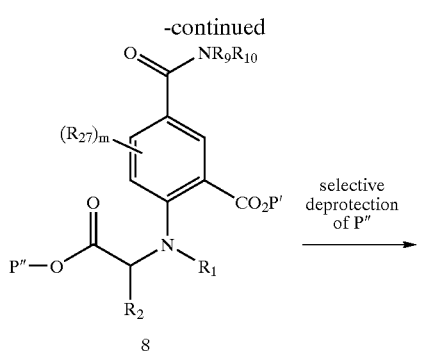

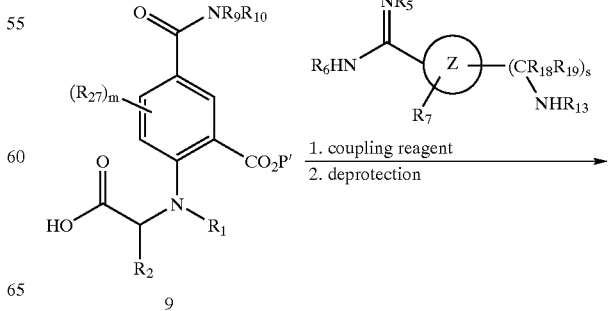

-continued

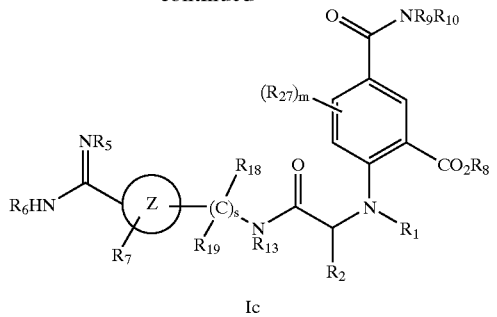

Ic

Aryl fluoride 3a is reacted with amine 7 in DMSO in the presence of a base such as DIEA to afford compound 8, where $R_3$ is defined as above except where $R_3$ and $R_4$ form a ring, said ring is a heterocyclo. Selective deprotection of the P" group affords acid 9. Reaction of acid 9 with an amidine $NHR_6C(=NR_7)-Z-(CR_{18}R_{19})_s-NHR_{13}$ in the presence of coupling reagent(s) such as DCC/HOBT/DMAP, EDC/DMAP, or DIC/HOAT affords the corresponding amidine compound which upon further optional deprotection, coupling or reaction (as described in Scheme A) affords the compound of formula Ic, having the desired group $R_8$. Further schemes for making Z group coupling components are described in U.S. patent application Ser. No. 10/052,927, being filed concomitantly herewith, having common inventors herein and assigned to the present assignee, which is incorporated herein by reference.

Utility

The inventive compounds are inhibitors of the activated coagulation serine proteases known as Factor VIIa, Factor IXa, Factor Xa, Factor XIa, and thrombin and also inhibit other serine proteases, such as trypsin, tryptase, and urokinase. Thus, the compounds are useful for treating or preventing those processes, which involve the production or action of Factor VIIa, Factor IXa, Factor Xa, Factor XIa, thrombin, trypsin, and/or tryptase. In view of their urokinase inhibitory activity, they are useful as metastasis inhibitors in treating cancer. As used herein with reference to the utilities described below, the term "treating" or "treatment" encompasses prevention, partial alleviation, or cure of the disease or disorder.

In view of their above-referenced serine protease inhibitory activity, the inventive compounds are useful in treating consequences of atherosclerotic plaque rupture including cardiovascular diseases associated with the activation of the coagulation cascade in thrombotic or thrombophilic states. Such diseases include arterial thrombosis, coronary artery disease, acute coronary syndromes, myocardial infarction, unstable angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

In addition, the inventive compounds are useful in preventing venous thrombosis, coagulation syndromes, deep vein thrombosis (DVT), disseminated intravascular coagulopathy, Kasabach-Merritt syndrome, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, $FV_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may also be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

In view of their tryptase inhibitory activity, the inventive compounds are useful as anti-inflammatory agents, in treating chronic asthma, allergic rhinitis, inflammatory bowel disease, psoriasis, conjunctivitis, atopic dermatitis, pancreatis, rheumatoid arthritis, osteoarthritis, septic shock, and chronic inflammatory joint diseases, diseases of joint cartilage destruction, and/or vascular damage due to bacterial and/or viral infections. Additionally, the inventive compounds may be useful for treating diabetic retinopathy or motor neuron diseases such as amyotrophic lateral sclerosis, progressive muscular atrophy, and primary lateral sclerosis. Additionally, the inventive compounds may be useful for tissue remodeling diseases and for treating plaque instability and sequelli. In addition, these compounds may be useful for treating fibrotic diseases and conditions, for example, fibrosis, scleroderma, pulmonary fibrosis, liver cirrhosis, myocardial fibrosis, neurofibromas, and hypertrophic scars.

In addition, the compounds of the present invention are useful in treating cancer and preventing the prothrombotic complications of cancer. In view of their metastasis inhibition activity, the compounds are useful in treating tumor growth, as an adjunct to chemotherapy, and for treating diseases involving metastases including, but not limited to cancer, more particularly, cancer of the lung, prostate, colon, breast, ovaries, and bone. These compounds may also be useful in preventing angiogenesis.

The inventive compounds may also be used in combination with other antithrombotic or anticoagulant drugs such as thrombin inhibitors, platelet aggregation inhibitors such as aspirin, clopidogrel, ticlopidine or CS-747, warfarin, low molecular weight heparins (such as LOVENOX), GPIIb/GPIIIa blockers, PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, itavastatin (Nissan/Kowa), and compounds disclosed in U.S. provisional application No. 60/211,594 filed Jun. 15, 2000, and No. 60/211,595 filed Jun. 15, 2000; microsomal triglyceride transport protein inhibitors (such as disclosed in U.S. Pat. Nos. 5,739,135, 5,712,279 and 5,760,246), antihypertensive agents such as angiotensin-converting enzyme inhibitors (e.g., captopril, lisinopril or fosinopril); angiotensin-II receptor antagonists (e.g., irbesartan, losartan or valsartan); and/or ACE/NEP inhibitors (e.g., omapatrilat and gemopatrilat); β-blockers (such as propranolol, nadolol and carvedilol), PDE inhibitors in combination with aspirin, ifetroban, picotamide, ketanserin, or clopidogrel and the like. The inventive compounds are also useful in combination with anti-arrhythmic agents such as for atrial fibrillation, for example, amiodarone or dofetilide.

The inventive compounds may be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like.

The inventive compounds may also be used in combination with β-adrenergic agonists such as albuterol, terbutaline, formoterol, salmeterol, bitolterol, pilbuterol, or fenoterol; anticholinergics such as ipratropium bromide; anti-inflammatory cortiocosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

The inventive compounds may also be useful in combination with other anticancer strategies and chemotherapies such as taxol and/or cisplatin.

The compounds may act synergistically with one or more of the above agents. For example, the inventive compounds may act synergistically with the above agents to prevent reocclusion following a successful thrombolytic therapy and/or reduce the time to reperfusion. Thus, reduced doses of thrombolytic agent(s) may be used, therefore minimizing potential hemorrhagic side effects.

The compounds of formula I or II may be administered by any means suitable for the condition to be treated, which may depend on the need for site-specific treatment or quantity of drug to be delivered. Systematic treatment is typically preferred for cancerous conditions, although other modes of delivery are contemplated. The compounds may be delivered orally, such as in the form of tablets, capsules, granules, powders, or liquid formulations including syrups; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of formula I or II may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

Enzyme Assays

Compound was prepared as a 5 mM stock in DMSO, diluted further in DMSO and added directly to the assays. The DMSO concentration for all these studies was less than 1% and compared to DMSO vehicle controls.

Human Factor VIIa was obtained from Enzyme Research Labs (Cat.# HFVIIA 1640). Human recombinant tissue factor (INNOVIN from Dade Behring Cat.# B4212-100; "20 ml vial") was diluted with 8 ml of $H_2O$ per vial and diluted further 1:30 into the 302 μl final assay volume. Tissue factor activated FVIIa enzymatic activity was measured in a buffer containing 150 mM NaCl, 5 mM $CaCl_2$, 1 mM CHAPS and 1 mg/ml PEG 6000 (pH 7.4) with 1 nM FVIIa and 100 μM D-Ile-Pro-Arg-AFC (Enzyme Systems Products, Km>200 μM) 0.66% DMSO. The assay (302 μl total volume) was incubated at RT for 2 hr prior to reading fluorometric signal (Ex 405/Em 535) using a Victor 2 (Wallac) fluorescent plate reader.

Human Factor IXa (American Diagnostica # 449b) enzymatic activity was measured in a buffer containing 50 mM Tris, 100 mM $CaCl_2$, 5 mM $CaCl_2$, 33% ethylene glycol at pH 7.5 using 96-well microtiter plates (Nunc # 439454). The enzyme was incubated with the inhibitor at RT for three minutes prior to starting the reaction with 500 uM Spectrozyme FIXa (American Diagnostica #299). The $K_m$ for this substrate is estimated by American Diagnostica to be 1.3 mM. Time dependent optical density change was followed at 405 nm using a kinetic microplate read (Molecular Devices Spectramax Plus) at RT. Enzyme activity in the presence of inhibitor was expressed as fraction of a DMSO-containing control and curve fit to the equation: activity=control activity/(1+[I]/$IC_{50}$) using Excel Fit.

Human FXa (Calbiochem #233526) enzymatic activity was measured in a buffer containing 0.145 M NaCl, 0.005 M KCl, 1 mg/ml Polyethylene Glycol (PEG-8000), 0.030 M HEPES (pH 7.4) using 96-well microtiter plates (Nunc Immuno #439454). The enzyme was incubated with the inhibitor at RT for three minutes prior to starting the reaction with 100 μM S-2222 (phenyl-Ile-Glu-Gly-Arg-pNA, $K_m$=137 μM). The $K_m$ for this and other substrates was determined experimentally by measuring the enzyme activity at different substrate concentrations and curve fitting the data using Kaleidagraph V. Time-dependent optical density change was followed at 405 nm using a kinetic microplate reader (Molecular Devices UVmax) at RT. Enzyme activity in the presence of inhibitor was expressed as fraction of a DMSO-containing control and curve fit to the equation: activity=control activity/(1+[I]/$IC_{50}$) using Excel Fit.

Recombinant urokinase (Abbott Labs, Abbokinase) was assayed in the same buffer as FXa, but the reactions were started with 100 μM S-2444 (L-pyroGlu-Gly-Arg-pNA, $K_m$=31 μM). Human α-thrombin (Sigma) was measured as for FXa except that the reaction was started with 10 μM S-2238 (D-Phe-Pip-Arg-pNA, $K_m$=2.54 μM).

Human FXIa assay (Enzyme Research Labs) was measured as for FXa except that the reaction was started with 100 μM S-2366 (L-pyroGlu-Pro-Arg-pNA, $K_m$=86 μM).

Bovine and human pancreatic trypsin (Sigma) were assayed in 2 mM $CaCl_2$, 50 mM Tris/Cl (pH 8.0) and the reaction was started with 100 μM Chromozym-TRY (Carboxybenzoxy-Val-Gly-Arg-pNA, $K_m$=46 μM).

Tryptase inhibition activity was measured using either isolated human skin tryptase or recombinant human tryptase prepared from the human recombinant beta-protryptase expressed by baculovirus in insect cells. The expressed beta-protryptase was purified using sequential immobilized heparin affinity resin followed by an immunoaffinity column using an anti-tryptase monoclonal antibody. The protryptase was activated by auto-catalytic removal of the N-terminal in the presence of dextran sulfate followed by dipeptidyl peptidase I (DPPI) removal of the two N-terminal amino acids to give the mature active enzyme (Sakai et al, *J. Clin. Invest.*, Vol. 97 (1996), at pp. 988–995). Essentially equivalent results were obtained using isolated native enzyme or the activated expressed enzyme. The tryptase enzyme was maintained in 2M sodium chloride, 10 nM 4-morpholinepropanesulfonic acid, pH 6.8. The assay procedure employed a 96 well microplate. To each well of the microplate (Nunc MaxiSorp), 250 μl of assay buffer [containing low molecular weight heparin and tris (hydroxymethyl) aminomethane] was added followed by 2.0 μl of the test compound in dimethylsulfoxide. The substrate (10 μl) was then added to each well to give a final concentration of 100 μM benzyloxycarbonyl-glycine-proline-arginine-p-nitroaniline (CBz-Gly-Pro-Arg-pNA). The microplate was then shaken on a platform vortex mixer at a setting of 800 (Sarstedt TPM-2). After a total of three minutes incubation, 10 μl of the working stock solution of tryptase was added to each well. The microplate was vortexed again for one minute and then incubated without shaking at RT for an additional 2 minutes. After this time the microplate was read on a microplate reader (Molecular Devices UV max) in the kinetic mode (405 nm wavelength) over twenty minutes at RT. To determine the compound concentration that inhibited half of the enzyme activity ($IC_{50}$), the fraction of control activity (FCA) was plotted as a function of the inhibitor concentration and curve to fit FCA/(1[I]/$IC_{50}$). The $IC_{50}$ for each compound was determined 2–4 times and the obtained values were averaged.

Applying the above-described assays, the inventive compounds demonstrated activity as inhibitors of Factor VIIa, IXa, Xa, XIa, tryptase and/or urokinase.

The following Examples illustrate embodiments of the inventive compounds and starting materials, and are not intended to limit the scope of the claims. For ease of reference, the following abbreviations are used herein:

ABBREVIATIONS

Me=methyl
Et=ethyl
Ph=phenyl
Bn=benzyl
t-Bu=tertiary butyl
Boc=tert-butoxycarbonyl
CBZ=carbobenzyloxy or carbobenzoxy or benzyloxycarbonyl
THF=tetrahydrofuran
EtOAc=ethyl acetate
DMF=dimethyl formamide
i-PrOH=isopropanol
DMSO=dimethyl sulfoxide
DME=1,2 dimethoxyethane
DCE=1,2 dichloroethane
AcOH=acetic acid
TFA=trifluoroacetic acid
i-$Pr_2$NEt=diisopropylethylamine
DMAP=4-dimethylaminopyridine
NMM=N-methyl morpholine
NaBH(OAc)$_3$=sodium triacetoxyborohydride
DCM=4-(dicyanomethylene)-2-methyl-6-(4-dimethylamino-styryl)-4H-pyran
Pd/C=palladium on carbon
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole Pd(OAc)$_2$=Palladium acetate
BINAP=2,2'-bis(diphenylphosphino)-1,1'-binaphthyl
CBZ-Cl=benzyl chloroformate
SAX=Strong Anion Exchanger
SCX=Strong Cation Exchanger
PVP=polyvinylpyridine
DCC=dicyclohexylcarbodiimide
DIC=diisopropylcarbodiimide
DMA=dimethyl acetamide
DIEA=diisopropylethylamine
DIPEA=diisopropylethylamine
DPPF=1,1'-bis(diphenylphosphino)ferrocene
TEA=triethylamine
TBS=t-butyldimethylsilyl
Tf=trifluoromethanesulfonyl
L=liter
mL=milliliter
μL=microliter
g=gram(s)
mg=milligram(s)
meq=milliequivalent
RT=room temperature
sat or sat'd=saturated
TLC=thin layer chromatography
HPLC=high performance liquid chromatography
LC/MS=high performance liquid chromatography/mass spectrometry
MS or Mass Spec=mass spectrometry
mp=melting point

EXAMPLE 1

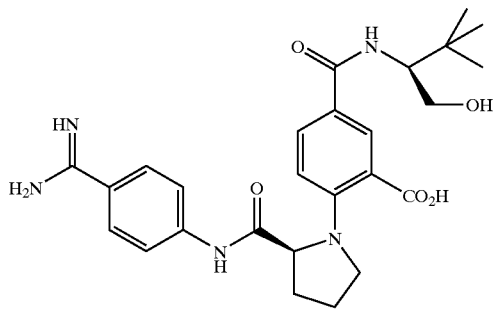

The compound of Example 1 was prepared following Steps A–D:

A.

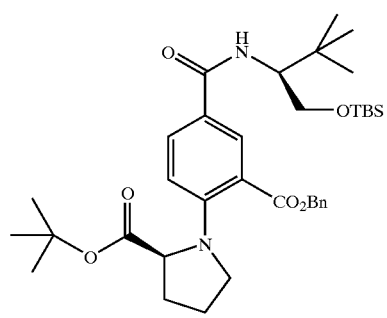

To a solution of

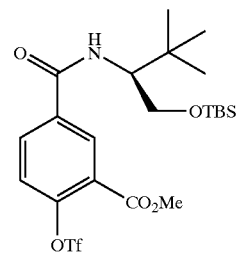

(100 mg, 0.162 mmol) in toluene (1.5 ml) under nitrogen were added L-proline t-butylester (40 mg, 0.234 mmol), Pd(OAc)$_2$ (2.3 mg), R-(+)-BINAP (9.6 mg) and lastly Cs$_2$CO$_3$ (83 mg). The reaction mixture was heated at 90° C for 66 hours. The reaction was diluted with methylene chloride:hexane (1:1, 8 ml) and loaded onto a silica gel cartridge (2 g). Flash chromatography with 0 to 15% EtOAc/hexane provided the above product (57 mg, 0.089 mmol) in 55% yield.

B.

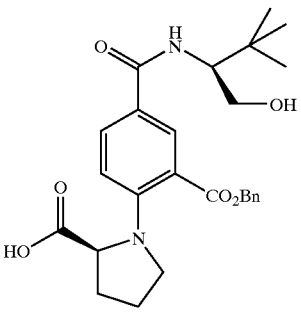

The product of Step A (57 mg, 0.089 mmol) was treated with 50%TFA/CH$_2$Cl$_2$ under nitrogen for 2 hours. Removal of solvents and drying under vacuum provided the desired hydroxy acid compound. This product also contained a side product wherein the hydroxymethyl group is trifluoroacetylated.

C.

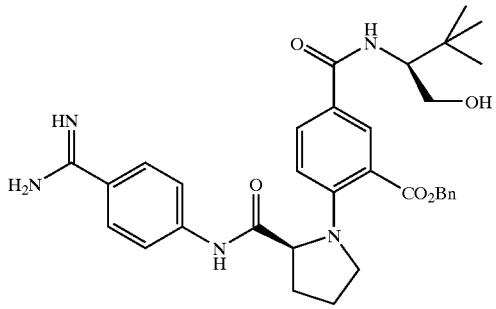

The combined products of Step B were dissolved in DMF:pyridine (1:1, 3 ml) under nitrogen and treated with DCC (36.7 mg, 0.178 mmol) and 4-aminobenzamidine.2HCl (74 mg, 0.356 mmol). The reaction mixture was heated to 50° C. for 2 hours. Solvents were removed under vacuum with warming to 40° C. Purification by preparative HPLC gave after removal of solvents the desired product (13 mg) and a side product wherein the hydroxymethyl group is trifluoroacetylated (7 mg).

D.

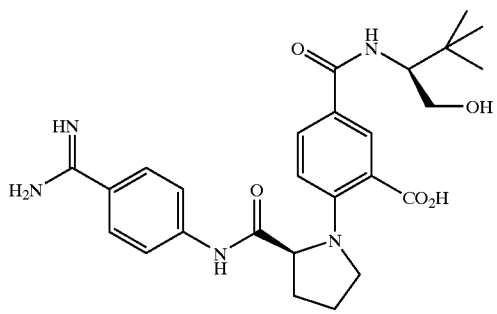

The combined products of Step C (20 mg) were dissolved in methanol (4 ml) and treated with hydrogen (1 atm, balloon) in the presence of 10%Pd/C (50 mg) for 30 minutes. NH$_4$OH (1.5 ml) was added to the reaction mixture, and the reaction mixture was filtered through a celite pad. Solvents were removed to provide the product of Example 1 (9.8 mg, MS: m/z 496 (M+H)$^+$) as a white solid.

EXAMPLES 2 AND 3

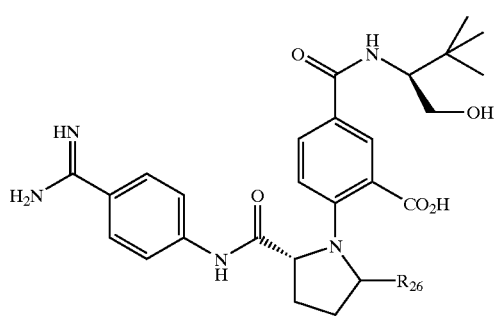

(If)

Examples 2 and 3 having formula (If) wherein R$_{26}$ is hydrogen (Example 2) and oxo (=O) (Example 3) were prepared in a similar manner as described above for Example 1.

EXAMPLES 3–8

Examples 3 through 8 are prepared in the same or similar manner as described above for Example 1 and in Schemes A–D.

| Example | Structure |
|---------|-----------|
| 8 | 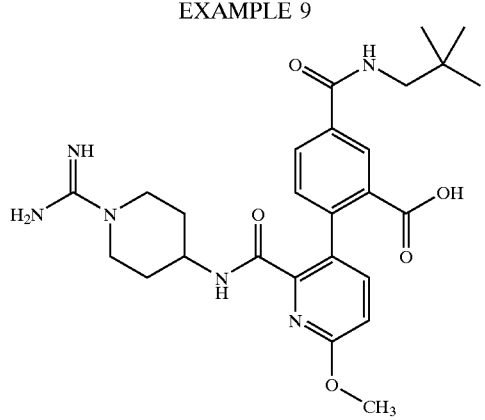 |

EXAMPLE 9

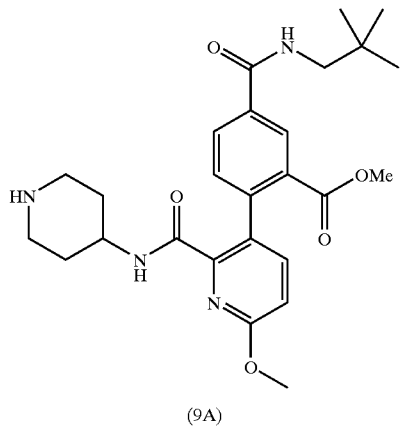

Step A:

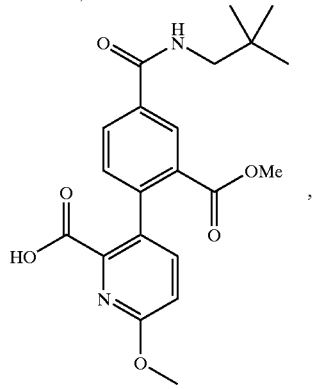

(9A)

75 mg (0.19 mmol) of Acid, 54 mg (0.28 mmol) EDAC, 4 mg (0.028 mmol) HOAT, and 3.5 mg (0.028 mmol) 4-DMAP were dissolved in 3 mL DCM and stirred at rt for ½ h. 57 mg (0.28 mmol) 4-amino-piperidine-1-carboxylic acid tert-butyl ester was dissolved in 1 mL N,N-DMF and added to the activated acid solution. The reaction stirred at rt overnight. MS, m/z (M+1)$^+$=583. 2 mL of TFA was added and the reaction was stirred for 3 h. MS, n/z (M+1)$^+$=483. The reaction was concentrated via speed vacuum and purified on prep HPLC to give 100 mg (92%) of the compound 9A.

Step B:

EXAMPLE 9

15 mg (0.031 mmol) of compound 9A and 8.5 mg (0.058 mmol) of 1H-pyrazole-1-carboxamidine hydrochloride were dissolved in 2 mL N,N-DMF and placed in an ice bath. 0.02 mL (0.093 mmol) DIPEA was added. The reaction was stirred at rt overnight. MS, m/z (M+1)$^+$=525. 2 mL 2M KOH in MeOH/H$_2$O was added to the reaction which was stirred at rt for 3 h. The reaction was concentrated on the speed vacuum and purified by prep HPLC to give 0.6 mg (4%) of Example 9 above. MS, m/z (M+1)$^+$=511.

We claim:

1. A compound having the formula (I),

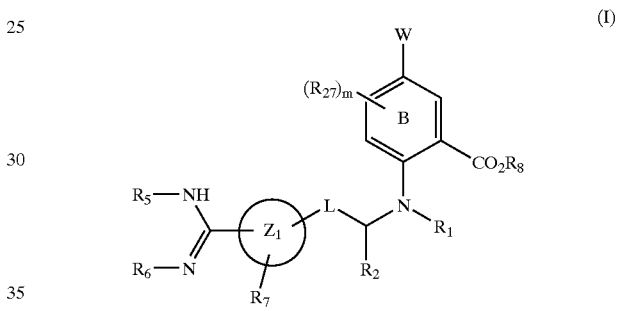

or a pharmaceutically-acceptable salt thereof, in which:

ring B is phenyl;

W is selected from $C_{2-10}$alkyl, $C_{2-10}$alkenyl, substituted $C_{2-10}$alkyl, substituted $C_{2-10}$alkenyl, —C(=O)NR$_9$R$_{10}$, —OR$_9$, —CO$_2$R$_9$, —C(=O)R$_9$, —SR$_9$, —S(O)$_p$R$_9$, —NR$_9$R$_{10}$, —NR$_9$SO$_2$R$_{10}$, —NR$_9$CO$_2$R$_{10}$, —NR$_9$C(=O)R$_{10}$, —SO$_2$NR$_9$R$_{10}$, heterocyclo, heteroaryl, aryl, and cycloalkyl;

$Z_1$ is a 5 to 7-membered monocyclic or 8 to 11-membered bicyclic aryl, heteroaryl, heterocyclo, or cycloalkyl;

L is —(CR$_{18}$R$_{19}$)$_s$—Y—(CR$_{18a}$R$_{19a}$)$_t$—;

Y is selected from —C(=O), —C(=O)NR$_{13}$—, —NR$_{13}$C(=O)—, —NR$_{13}$CR$_{14}$R$_{15}$—, —CR$_{14}$R$_{15}$—NR$_{13}$—, and —CR$_{13}$R$_{14}$—CR$_{15}$R$_{16}$—;

R$_1$ and R$_2$ are taken together to form a five-to-seven membered fully saturated heterocycle containing N, and optionally substituted with one to two R$_{26}$;

R$_5$ and R$_6$ are independently selected from hydrogen, alkyl, substituted alkyl, hydroxy, alkoxy, substituted alkoxy, —C(=O)H, acyl, —CO$_2$H, and alkoxycarbonyl, provided that at least one of R$_5$ and R$_6$ is hydrogen;

R$_7$ is attached to any available carbon or nitrogen atom of Z$_1$ and is selected from hydrogen, halogen, alkyl, substituted alkyl, alkenyl, substituted alkenyl, alkynyl, substituted alkynyl, heteroalkyl, substituted heteroalkyl, —C(=O)H, acyl, —CO$_2$H, alkoxycarbonyl, sulfonyl, sulfonamido, aryl, heteroaryl, heterocyclo, or cycloalkyl, except when Z is phenyl, W is OCH$_3$, s is 0 and Y is —CH$_2$—CH$_2$—, then R$_7$ is not phenyloxy;

$R_8$ is hydrogen, alkyl, substituted alkyl, heteroaryl, aryl, heterocyclo, cycloalkyl, or alkyl substituted with —OC(=O)$R_{24}$ or —OC(=O)O—$R_{24}$, wherein $R_{24}$ is alkyl, substituted alkyl, or cycloalkyl, provided that $R_8$ is not phenyl when W is methoxy;

$R_9$, $R_{9a}$, and $R_{10}$ are (i) independently selected from hydrogen, alkyl, alkenyl, alkynyl, heteroalkyl, substituted heteroalkyl, aryl, heteroaryl, heterocyclo, cycloalkyl, and alkyl having one, two, or three substituents selected from the group consisting of halo, alkenyl, alkynyl, nitro, cyano, hydroxy, alkoxy, alkylthio, —$CO_2H$, —C(=O)H, —$CO_2$-alkyl, —C(=O)alkyl, —S(O)$_2$(alkyl), keto (=O), aryl, heteroaryl, heterocyclo, and cycloalkyl, including phenyl, benzyl, phenylethyl, phenyloxy, and phenylthio; or alternatively (ii) $R_9$ and $R_{10}$ may be taken together to form a five-to-seven membered heteroaryl or heterocyclo, except when W is —S(O)$_p$$R_9$, then $R_9$ is not hydrogen;

$R_{13}$, $R_{14}$, $R_{15}$, $R_{16}$, $R_{18}$, $R_{18a}$, $R_{19}$, and $R_{19a}$ are selected from hydrogen, lower alkyl, hydroxy, or lower alkyl substituted with hydroxy or halogen;

$R_{26}$ and $R_{27}$ (i) are at each occurrence independently selected from hydrogen, $OR_{30}$, $NR_{31}R_{32}$, $NR_{31}SO_2R_{32a}$, alkyl, alkenyl, substituted alkyl, substituted alkenyl, halogen, haloalkyl, haloalkoxy, cyano, nitro, alkylthio, —C(=O)H, acyl, —$CO_2H$, alkoxycarbonyl, sulfonamido, sulfonyl, and phenyl, or (ii) two of $R_{26}$ and/or two of $R_{27}$ may be taken together to form a fused benzo ring, a fused heteroaryl, a fused cycloalkyl, or a fused heterocyclo other than a five or six membered heterocyclo having as its heteroatoms two oxygen atoms;

$R_{30}$ at each occurrence is selected from hydrogen, alkyl, substituted alkyl, alkenyl, substituted alkenyl, cycloalkyl, and phenyl;

$R_{31}$ and $R_{32}$ at each occurrence are independently selected from hydrogen, alkyl, substituted alkyl, alkenyl, substituted alkenyl, and cycloalkyl;

$R_{32a}$ is alkyl, substituted alkyl, alkenyl, substituted alkenyl, or cycloalkyl;

m is 0, 1 or 2 when ring B is phenyl and 0 or 1 when ring B is pyridyl;

p and q are independently 1 or 2; and s and t are independently 0, 1 or 2.

2. A compound having the formula (I),

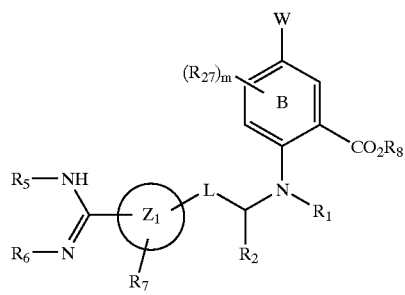

(I)

or a pharmaceutically-acceptable salt thereof, in which
ring B is phenyl;
W is —C(=O)NHCH($R_{25}$)-t-butyl or —$CH_2$C(=O)NHCH($R_{25}$)-t-butyl;
$Z_1$ is a 5 to 7-membered monocyclic or 8 to 11-membered bicyclic aryl, heteroaryl, heterocyclo, or cycloalkyl;

L is —C(=O)—, —NHC(=O)—, or —NH—$CH_2$—;

$R_1$ and $R_2$ are taken to together to form a five-to-seven membered fully saturated heterocycle containing N, and optionally substituted with one to two $R_{26}$;

$R_5$, $R_6$ and $R_7$ are hydrogen;

$R_8$ is hydrogen, alkyl, substituted alkyl, heteroaryl, aryl, heterocyclo, cycloalkyl, or alkyl substituted with —OC(=O)$R_{24}$ or —OC(=O)O—$R_{24}$ wherein $R_{24}$ is alkyl, substituted alkyl, or cycloalkyl, provided that $R_8$ is not phenyl when W is methoxy;

$R_{25}$ is hydrogen or hydroxymethyl;

$R_{26}$ and $R_{27}$ (i) are at each occurrence independently selected from hydrogen, $OR_{30}$; $NR_{31}R_{32}$, $NR_{31}SO_2R_{32a}$, alkyl, alkenyl, substituted alkyl, substituted alkenyl, halogen, haloalkyl, haloalkoxy, cyano, nitro, alkylthio, —C(=O)H, acyl, —$CO_2H$, alkoxycarbonyl, sulfonamido, sulfonyl, and phenyl, or (ii) two of $R_{26}$ and/or two of $R_{27}$ may be taken together to form a fused benzo ring, a fused heteroaryl, a fused cycloalkyl, or a fused heterocyclo other than a five or six membered heterocyclo having as its heteroatoms two oxygen atoms;

$R_{30}$ at each occurrence is selected from hydrogen, alkyl, substituted alkyl, alkenyl, substituted alkenyl, cycloalkyl, and phenyl;

$R_{31}$ and $R_{32}$ at each occurrence are independently selected from hydrogen, alkyl, substituted alkyl, alkenyl, substituted alkenyl and cycloalkyl;

$R_{32a}$ is alkyl, substituted alkyl, alkenyl, substituted alkenyl, or cycloalkyl;

m is 0, 1 or 2 when ring B is phenyl and 0 or 1 when ring B is pyridyl;

p and q are independently 1 or 2; and s and t are independently 0, 1 or 2.

3. The compound of claim 2, having the formula:

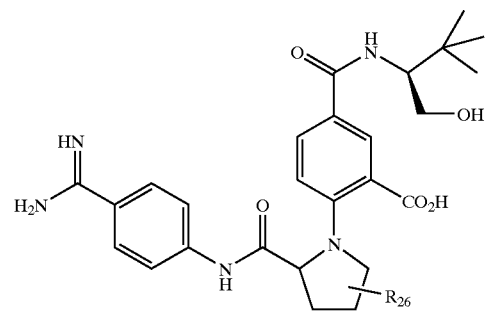

or a pharmaceutically-acceptable salt, thereof.

4. A pharmaceutical composition comprising (a) one compound according to claim 1, or a pharmaceutically acceptable salt thereof, and (b) a pharmaceutically acceptable carrier or diluent.

5. A pharmaceutical composition for treating metastasis comprising (a) one compound according to claim 1, or a pharmaceutically acceptable salt, thereof, and (b) a pharmaceutically acceptable carrier or diluent.

6. A pharmaceutical composition comprising (a) one compound according to claim 2, or a pharmaceutically acceptable salt, thereof, and (b) a pharmaceutically acceptable carrier or diluent.

7. A pharmaceutical composition comprising (a) one compound according to claim 3, or a pharmaceutically acceptable salt, thereof, and (b) a pharmaceutically acceptable carrier or diluent.

8. A pharmaceutical composition for treating metastasis comprising (a) one compound according to claim 2, or a pharmaceutically acceptable salt, thereof, and (b) a pharmaceutically acceptable carrier or diluent.

9. A pharmaceutical composition for treating metastasis comprising (a) one compound according to claim 3, or a pharmaceutically acceptable salt, thereof, and (b) a pharmaceutically acceptable carrier or diluent.

* * * * *